(12) United States Patent
Tumey et al.

(10) Patent No.: US 9,545,302 B2
(45) Date of Patent: Jan. 17, 2017

(54) SKIN PRINTING AND AUTO-GRAFTING (71) Applicant: Innovative Therapies, Inc., Gaithersburg, MD (US)

(72) Inventors: David Tumey, Gaithersburg, MD (US); Sandra Berriman, Gaithersburg, MD (US)

(73) Assignee: DermaGenesis LLC, Miami, FL (US)

( * ) Notice: Subject to any disclaimer, the term of this patent is extended or adjusted under 35 U.S.C. 154(b) by 212 days.

(21) Appl. No.: 14/084,896

(22) Filed: Nov. 20, 2013

(65) Prior Publication Data
US 2015/0139960 A1 May 21, 2015

(51) Int. Cl.
*A61F 2/10* (2006.01)
*A61F 2/02* (2006.01)
*A61L 27/56* (2006.01)
*B29C 67/00* (2006.01)
*C12N 5/071* (2010.01)
*B33Y 10/00* (2015.01)
*B33Y 50/00* (2015.01)
*A61L 27/22* (2006.01)
*A61L 27/36* (2006.01)
*A61L 27/60* (2006.01)
*A61K 35/36* (2015.01)

(52) U.S. Cl.
CPC .............. *A61F 2/105* (2013.01); *A61L 27/227* (2013.01); *A61L 27/362* (2013.01); *A61L 27/3604* (2013.01); *A61L 27/3691* (2013.01); *A61L 27/60* (2013.01); *B29C 67/0055* (2013.01); *B29C 67/0088* (2013.01); *B33Y 10/00* (2014.12); *B33Y 50/00* (2014.12); *C12N 5/0625* (2013.01); *C12N 5/0698* (2013.01); *A61F 2210/0004* (2013.01); *A61F 2230/0017* (2013.01); *A61F 2240/002* (2013.01); *A61K 35/36* (2013.01); *A61L 2300/412* (2013.01); *A61L 2300/64* (2013.01); *A61L 2430/34* (2013.01); *C12N 2513/00* (2013.01)

(58) Field of Classification Search
CPC .... A61F 2240/002; A61F 2/105; A61L 27/60; A61L 2300/412; A61L 2300/64; A61L 2430/34; A61L 27/3604; A61L 27/362; A61L 27/3691; A61L 27/3813; A61L 27/58; B33Y 10/00; B33Y 50/00; B33Y 80/00
USPC .......... 424/93.7, 400, 423; 623/11.11, 15.12, 623/23.75
See application file for complete search history.

(56) References Cited

U.S. PATENT DOCUMENTS

| 5,292,655 | A | 3/1994 | Wille |
|---|---|---|---|
| 5,639,654 | A | 6/1997 | Bernard et al. |
| 5,667,961 | A | 9/1997 | Bernard et al. |
| 5,686,307 | A | 11/1997 | Wille |
| 5,698,228 | A | 12/1997 | Takai et al. |
| 5,795,781 | A | 8/1998 | Wille |
| 6,010,701 | A | 1/2000 | Matsukura et al. |
| 6,262,255 | B1 | 7/2001 | Mares-Guia |
| 6,846,675 | B2 | 1/2005 | Conrad et al. |
| 6,858,222 | B2 | 2/2005 | Nelson et al. |
| 7,172,417 | B2 | 2/2007 | Sporbert et al. |
| 7,198,641 | B2 | 4/2007 | Barrows et al. |
| 7,261,542 | B2 | 8/2007 | Hickerson et al. |
| 7,286,679 | B2 | 10/2007 | Fang et al. |
| 7,291,364 | B2 | 11/2007 | Faulkner et al. |
| 7,335,377 | B2 | 2/2008 | Stern et al. |
| 7,353,153 | B2 | 4/2008 | Ascenzi et al. |
| 7,363,075 | B2 | 4/2008 | Stern et al. |
| 7,369,915 | B2 | 5/2008 | Kritchman et al. |
| 7,383,084 | B2 | 6/2008 | Stern et al. |
| 7,384,786 | B2 | 6/2008 | Freyman et al. |
| 7,514,095 | B2 | 4/2009 | Nelson et al. |
| 7,537,754 | B2 | 5/2009 | Devore et al. |
| 7,541,188 | B2 | 6/2009 | Conrad et al. |
| 7,550,518 | B2 | 6/2009 | Bredt et al. |
| 7,579,189 | B2 | 8/2009 | Freyman et al. |
| 7,589,868 | B2 | 9/2009 | Velde et al. |
| 7,651,507 | B2 | 1/2010 | Mishra et al. |
| 7,651,682 | B2 | 1/2010 | Devore et al. |
| 7,651,683 | B2 | 1/2010 | Devore et al. |
| 7,658,976 | B2 | 2/2010 | Kritchman et al. |
| 7,662,404 | B2 | 2/2010 | Stern et al. |
| 7,686,989 | B2 | 3/2010 | Van der Zel et al. |
| 7,699,606 | B2 | 4/2010 | Sachdeva et al. |
| 7,708,557 | B2 | 5/2010 | Rubbert et al. |
| 7,713,048 | B2 | 5/2010 | Perret et al. |
| 7,792,341 | B2 | 9/2010 | Schutyser |
| 7,807,077 | B2 | 10/2010 | Hochsmann et al. |
| 7,815,931 | B2 | 10/2010 | Woodroof et al. |

(Continued)

OTHER PUBLICATIONS

Hybbinette et al., "Enzymatic dissociation of keratinocytes from human skin biopsies for in vitro cell propagation", Exp Dermatol., Feb. 1999, pp. 30-38, vol. 8, No. 1.

Hutmacher, "Scaffold design and fabrication technologies for engineering tissues—state of the art and future perspectives", J Biomater. Sci. Polymer EDN, 2001, pp. 107-124, vol. 12, No. 1.

Priya et al., "Skin Tissue Engineering for Tissue Repair and Regeneration", Tissue Engineering: Part B, 2008, pp. 105-118, vol. 14, No. 1.

Schultz et al., "Interactions between extracellular matrix and growth factors in wound healing", Wound Rep Reg, 2009, pp. 153-162, vol. 17.

(Continued)

*Primary Examiner* — Janet Epps-Smith
(74) *Attorney, Agent, or Firm* — Witham, Curtis & Cook, P.C.

(57) ABSTRACT

An apparatus and method for the production of substitute skin that advantageously reduces the amount of donor dermal cells needed from non-wound areas of a patient having a wound to be auto-grafted is reduced by using all of the harvested skin cells. A 3D printer is used to construct a wound graft product from the harvested skin cells without wasting any of the harvested skin cells. In a case of an irregularly shaped wound, wastage of harvested skin associated with trimming is avoided.

8 Claims, 3 Drawing Sheets

(56) References Cited

U.S. PATENT DOCUMENTS

| | | | |
|---|---|---|---|
| 7,879,393 B2 | 2/2011 | Ederer et al. | |
| 8,021,154 B2 | 9/2011 | Holzner et al. | |
| 8,048,671 B2 | 11/2011 | Hendriks et al. | |
| 8,071,007 B1 | 12/2011 | Teoh et al. | |
| 8,071,083 B2 | 12/2011 | Bruijn et al. | |
| 8,086,336 B2 | 12/2011 | Christensen et al. | |
| 8,095,210 B2 | 1/2012 | Burdick et al. | |
| 8,095,382 B2 | 1/2012 | Boyden et al. | |
| 8,100,692 B2 | 1/2012 | Diangelo et al. | |
| 8,114,859 B2 | 2/2012 | DeLuca et al. | |
| 8,119,053 B1 | 2/2012 | Bedal et al. | |
| 8,133,505 B2 | 3/2012 | Stern et al. | |
| 8,133,831 B2 | 3/2012 | Laubersheimer et al. | |
| 8,147,537 B2 | 4/2012 | Boyden et al. | |
| 8,150,145 B2 | 4/2012 | Lemelin et al. | |
| 8,175,734 B2 | 5/2012 | Fogel et al. | |
| 8,186,990 B2 | 5/2012 | Perret et al. | |
| 8,206,152 B2 | 6/2012 | Holzner et al. | |
| 8,224,006 B2 | 7/2012 | Beck et al. | |
| 8,243,334 B2 | 8/2012 | Abeloe et al. | |
| 8,260,589 B1 | 9/2012 | Kumar et al. | |
| 8,287,854 B2 | 10/2012 | Phan et al. | |
| 8,337,554 B2 | 12/2012 | Miura et al. | |
| 8,366,432 B2 | 2/2013 | Perret et al. | |
| 8,366,789 B2 | 2/2013 | Summit et al. | |
| 8,394,371 B2 | 3/2013 | Laurent-Applegate et al. | |
| 8,485,820 B1 | 7/2013 | Ali et al. | |
| 8,506,870 B2 | 8/2013 | Hochsmann et al. | |
| 8,521,319 B2 | 8/2013 | Schmidt et al. | |
| 8,524,312 B2 | 9/2013 | Huda et al. | |
| 8,528,717 B2 | 9/2013 | Ando et al. | |
| 8,543,234 B2 | 9/2013 | Geo et al. | |
| 8,552,100 B2 | 10/2013 | Song et al. | |
| 8,556,983 B2 | 10/2013 | Bojarski et al. | |
| 8,562,324 B2 | 10/2013 | Pettis et al. | |
| 8,565,909 B2 | 10/2013 | Bickel et al. | |
| 2002/0164793 A1 | 11/2002 | Conrad et al. | |
| 2004/0029478 A1 | 2/2004 | Planck et al. | |
| 2004/0126878 A1 | 7/2004 | Ramos et al. | |
| 2005/0226853 A1 | 10/2005 | Conrad et al. | |
| 2009/0230592 A1 | 9/2009 | Woodroof | |
| 2009/0232878 A1 | 9/2009 | Woodroof et al. | |
| 2009/0234305 A1 | 9/2009 | Woodroof | |
| 2010/0000676 A1 | 1/2010 | Woodroof | |
| 2010/0318108 A1 | 12/2010 | Datta et al. | |
| 2011/0098815 A1 | 4/2011 | Miura et al. | |
| 2011/0159582 A1 | 6/2011 | Israelowitz et al. | |
| 2011/0165130 A1 | 7/2011 | Guenou | |
| 2011/0171180 A1 | 7/2011 | Bush et al. | |
| 2011/0172611 A1 | 7/2011 | Yoo et al. | |
| 2011/0281771 A1 | 11/2011 | Chernokalskaya et al. | |
| 2012/0022472 A1 | 1/2012 | Miura et al. | |
| 2012/0109300 A1 | 5/2012 | Miura et al. | |
| 2013/0209427 A1 | 8/2013 | Thangapazham et al. | |
| 2014/0228970 A1* | 8/2014 | Boland | 623/23.72 |

OTHER PUBLICATIONS

Karaaltin et al., "Adipose Derived Regenerative Cell Therapy for Treating a Diabetic Wound: A Case Report", Oct. 6, 2011, Web.
Rosenblatt, "Researchers aim to 'print' human skin", CNN, Feb. 15, 2011, Web.
Kirsner et al., "Spra-applied cell therapy with human allogeneic fibroblasts and kertinocytes for the treatment of chronic venous leg ulcers: a phase 2, multicentre, double-blind, randomised, placebo-controlled trial", The Lancet, Sep. 15, 2012, pp. 977-985, vol. 380.
Raelin, "Wake Forest 3d Prints Skin Cells Onto Burn Wounds", 3D Printer World, Jul. 19, 2012, Web.
Lutz, "Printed Skin Cells Will Change How We Treat Burns Forever", Business Insider, Aug. 3, 2012, Web.
Anonymous, Printing Skin, Medical Discovery News, Web.
Zelen et al., "A prospective randomised comparative parallel study of amniotic membrane wound graft in the management of diabetic foot ulcers", International Wound Journal, 2013.
Kim et al., "Evaluation of an Amniotic Membrane-Collagen Dermal Substitute in the Management of Full-Thickness Skin Defects in a Pig", Archives of Plastic Surgery, 2013, pp. 11-18, vol. 40, No. 1.
"SkinPrint: 3D Bio-printed human skin can help burn victims", 3DERS, May 16, 2013, Web.
Maxey, "3D Printed, Transplantable Skin in 5 Years?" Engineering, May 17, 2013, Web.
Briggs, "Artificial human ear grown in lab", BBC, Jul. 31, 2013, Web.
Leckart, "How 3-D Printing Body Parts Will Revolutionize Medicine", Popular Science, Aug. 6, 2013, Web.
Liu et al., "Techniques for fabrication and construction of three-dimensional scaffolds for tissue engineering", Internat'l Journal of Nanomedicine, 2013, pp. 337-350, vol. 8.
Paulsson, "Basement Membrane Proteins: Structure, Assembly, and Cellular Interactions", Critical Reviews in Biochemistry and Molecular Biology, 1992, pp. 93-127, vol. 27.
Clark, "Bioengineer: the heart is one of the easiest organs to bioprint, we'll do it in a decade", Wired, Nov. 21, 2013, Web.
Chen et al., "Culturing of skin fibroblasts in a thin PLGA-collagen hybrid mesh", Biomaterials, 2005, pp. 2559-2566, vol. 26.
Jayo et al., "Early Cellular and Stromal Responses in Regeneration Versus Repair of a Mammalian Bladder Using Autologous Cell and Biodegradeable Scaffold Technologies", Journal of Urolog, 2008, pp. 392-397, vol. 180.
Goldstein, "Selecting the right mesh", Hernia, 1999, pp. 23-26, vol. 3.

\* cited by examiner

SKIN PRINTING AND AUTO-GRAFTING

FIELD OF THE INVENTION

The invention relates to the medical arts, more particularly, to tissue engineering especially tissue engineering in which three-dimensional printing technology is used.

BACKGROUND OF THE INVENTION

Healing wounds is a complex process of tissue repair and regeneration in response to injury. The healing response in skin wounds attempts to reconstitute a tissue similar to the original damaged one and this is accomplished via the concerted action of numerous skin cell types, collagens, cytokines, growth factors (GF s), chemokines, cell surface and adhesion molecules, as well as multiple extracellular matrix proteins. Autologous split-thickness skin grafting currently represents the most rapid, effective method of reconstructing large skin defects; however, in cases where a significant quantity of harvested graft is required, it represents yet another trauma to an already injured patient.

Some patent literature and academic literature is mentioned as follows, generally in roughly chronological order:

Wille, Jr., "Method for the formation of a histologically-complete skin substitute," U.S. Pat. No. 5,292,655 issued Mar. 8, 1994;

Bernard, et al., "Process for creating a skin substitute and the resulting skin substitute," U.S. Pat. No. 5,639,654 issued Jun. 17, 1997;

Bernard et al., "Skin substitute," U.S. Pat. No. 5,667,961 issued Sep. 16, 1997;

Wille, Jr., "Serum free medium for use in the formation of a histologically complete living human skin substitute," U.S. Pat. No. 5,686,307 issued Nov. 11, 1997;

Takai et al., "Wound healing composition using squid chitin and fish skin collagen," U.S. Pat. No. 5,698,228 issued Dec. 16, 1997;

Wille, Jr., "Cell competency solution for use in the formation of a histologically-complete, living, human skin substitute," U.S. Pat. No. 5,795,781 issued Aug. 18, 1998;

S. Hybbinette et al., "Enzymatic dissociation of keratinocytes from human skin biopsies for in vitro cell propagation," *Exp Dermatol.*, 1999: February; 8(1):30-8;

Mares-Guia, "Non-immunogenic, biocompatible macromolecular membrane compositions, and methods for making them," U.S. Pat. No. 6,262,255 issued Jul. 17, 2001;

D. W. Hutmacher, "Scaffold design and fabrication technologies for engineering tissues—state of the art and future perspectives," *J. Biomater. Sci. Polymer Edn*, 12:1, 107-124 (2001);

Conrad et al., "Skin substitutes and uses thereof," US 20020164793 published Nov. 7, 2002;

Ramos et al., "Method for the preparation of immunologically inert amniotic membranes," US 20040126878 published Jul. 1, 2004;

Conrad et al., "Skin substitutes and uses thereof," U.S. Pat. No. 6,846,675 issued Jan. 25, 2005;

Conrad et al., "Skin substitutes and uses thereof," US 20050226853 published Oct. 13, 2005;

S. G. Priya, et al., "Skin Tissue Engineering for Tissue Repair and Regeneration," *Tissue Engineering*: Part B, 14:1, 2008, 105-118;

G. S. Schultz, et al., "Interactions between extracellular matrix and growth factors in wound healing," *Wound Rep Reg* 17, 153-162 (2009);

Conrad et al., "Skin substitutes and uses thereof," U.S. Pat. No. 7,541,188 issued Jun. 2, 2009;

Woodroof, "Laser-Perforated Skin Substitute," US 20090230592 published Sep. 17, 2009;

Woodroof, et al., "Artificial Skin Substitute," US 20090232878 published Sep. 17, 2009;

Woodroof; "Temporary Skin Substitute comprised of biological compounds of plant and animal origins," US 20090234305 published Sep. 17, 2009;

Woodroof, et al., "Skin Substitute Manufacturing Method," US 20100000676 published Jan. 7, 2010;

Woodroof, et al., "Artificial skin substitute," U.S. Pat. No. 7,815,931 issued Oct. 19, 2010;

Mirua, et al., "Skin Substitute Membrane, Mold, and Method of Evaluating External Preparation for Skin," US 20110098815 published Apr. 28, 2011;

Israelowitz et al., "Apparatus for the growth of artificial organic items, especially human or animal skin," US 20110159582 published Jun. 30, 2011;

Guenou, "Methods for Preparing Human Skin Substitutes from Human Pluripotent Stem Cells," US 20110165130 published Jul. 7, 2011;

Bush et al., "Bioengineered Skin Substitutes," US 20110171180 published Jul. 14, 2011;

Yoo et al., "Delivery system," US 20110172611 published Jul. 14, 2011;

M. V. Karaaltin et al., "Adipose Derived Regenerative Cell Therapy for Treating a Diabetic Wound: A Case Report," Oct. 6, 2011;

Chernokalskaya, et al., "Polymeric Membranes with Human Skin-like Permeability Properties and uses thereof," US 20110281771 published Nov. 17, 2011;

Miura et al., "Application method of external dermatological medications, evaluating method of the same, application evaluating apparatus, and application evaluating program," US 20120022472 published Jan. 26, 2012;

D. Rosenblatt, "Researchers aim to 'print' human skin," Feb. 15, 2011, www.cnn.com;

Miura et al., "Skin substitute membrane, mold, and method of evaluating external preparation for skin," US 20120109300 published May 3, 2012;

R. Kirsner, et al., "Spray-applied cell therapy with human allogeneic fibroblasts and kertinocytes for the treatment of chronic venous leg ulcers: a phase 2, multicentre, double-blind, randomised, placebo-controlled trial," www.thelancet.com, vol. 380, Sep. 15, 2012;

B. Raelin, "Wake Forest 3D Prints Skin Cells Onto Burn Wounds," Jul. 19, 2012, www.3dprinter-world.com;

A. Lutz, "Printed Skin Cells Will Change How We Treat Burns Forever", Aug. 3, 2012, www.businessinsider.com;

Miura et al., "Skin substitute membrane, mold, and method of evaluating external preparation for skin," U.S. Pat. No. 8,337,554 issued Dec. 25, 2012;

"Printing Skin," www.medicaldiscoverynews.com/shows/202_printSkin.html, undated;

C. M. Zelen, et al., "A prospective randomised comparative parallel study of amniotic membrane wound graft in the management of diabetic foot ulcers," *International Wound Journal*, ISSN 1742-4801, 2013;

H. Kim, et al., "Evaluation of an Amniotic Membrane-Collagen Dermal Substitute in the Management of Full-Thickness Skin Defects in a Pig," *Archives of Plastic Surgery*, 2013, 40:1, 11-18;

"SkinPrint: 3D Bio-printed human skin can help burn victims", May 16, 2013, www.3ders.org;

K. Maxey, "3D Printed, Transplantable Skin in 5 Years?", May 17, 2013, www.engineering.com;

H. Briggs, "Artificial human ear grown in lab," Jul. 31, 2013, www.bbc.co.uk;

S. Leckart, "How 3-D Printing Body Parts Will Revolutionize Medicine," Aug. 6, 2013, www.popsci.com;

Thangapazham et al., "Hair follicle neogenesis," US 20130209427 published Aug. 15, 20131

T. Lu et al., "Techniques for fabrication and construction of three-dimensional scaffolds for tissue engineering," *Internat'l Journal of Nanomedicine*, 2013:8, 337-350.

Although there are a number of reports of skin autografts produced in vitro, they take weeks to generate—which is too long a waiting period for a patient whose wound needs treatment. Quicker production of skin autografts is an unmet need and unsolved problem.

In several studies conducted using amniotic membrane (AM) in both acute and chronic wounds, much of the first round placement is absorbed into the body. In some cases, it takes as many of 3-4 full grafts of AM in order to result in full closure of the wound. Less graft being absorbed into the body so that it is unable to contribute to closing the wound is an unsolved problem.

Another difficult unsolved problem has been that when an undamaged donor area of skin of a patient is harvested and used as an autograft for treating the patient's own wound, the donor site often becomes a non-healing wound.

There are complicated, unsolved problems and unmet needs for better technologies in wound grafting and wound healing.

SUMMARY OF THE INVENTION

The invention addresses the above-described problems by processing ALL of the harvested skin cells taken from a healthy donor site on the patient with the wound to construct a customized skin graft product to be auto-grafted onto the wound. Production of a customized skin graft preferably is accomplished by operation of a three-dimensional ("3D") printer, which is supplied with substrate material and autologous skin cells and "prints" the supplied skin cells onto an agar plate or other surface.

Advantageously the amount of donor dermal cells needed from non-wound areas of a patient having a wound to be auto-grafted is reduced by using all of the harvested skin cells. A 3D printer is used to construct a wound graft product from the harvested skin cells without wasting any of the harvested skin cells. In a case of an irregularly shaped wound, wastage of harvested skin associated with trimming is avoided. The invention's provision of a skin grafting method that requires only the least amount of precious skin of the donor site to be damaged is highly important given major functions of skin: acting as a protective barrier from environmental insults including trauma, radiation, harsh environmental conditions and infection, providing thermo-regulation (through sweating, vasoconstriction or vasodilation) and controlling fluid loss. This minimization of skin damage provided by the invention, in addition to the ability to continually regenerate the necessary skin until healing is complete, represent major advances in wound care.

A major objective of the invention is to use the patient's own skill cells to re-create a strong, persistent organ replacement solution.

The invention in a preferred embodiment provides a computerized skin printing system, comprising: a quantity of living donor skin cells harvested from a non-wound area of a patient having a to-be-treated wound or tissue defect; a three-dimensional printer that processes the quantity of living donor skin cells harvested from a non-wound area of a patient having the wound or tissue defect, wherein the three-dimensional printer is under control of a controller connected to the three-dimensional printer; an imaging device (such as, e.g., an imaging device that comprises a camera; an imaging device that comprises a video camera; an imaging device that comprises a hand-held device; an imaging device that is movable to be positioned relative to the wound being imaged; etc.); and a computer that performs steps of receiving a set of images (such as, e.g., a set of one wound image; a set of multiple images) taken by the imaging device of the wound or tissue defect and processing the imaged wound or tissue defect into a set of skin-printing instructions that are provided to the controller connected to the three-dimensional printer; such as, e.g., a skin printing system further comprising a sizing grid that is projected onto the wound or tissue defect while the imaging device is being operated; a skin printing system further comprising a monitor connected to the computer; a skin printing system further comprising a keyboard connected to the computer; a skin printing system further comprising at least one syringe pump (such as e.g., a syringe pump that contains the quantity of living donor skin cells harvested from the non-wound area) under control of the controller; a skin printing system further comprising a surface onto which the three-dimensional printer prints a skin product (such as, e.g., a skin printing system wherein the skin product printed onto the surface corresponds to a model generated by the computer from the set of wound images); a skin printing system further comprising a pump, and wherein skin cells in a syringe are pumped by the pump into the three-dimensional printer; a skin printing system wherein the computer digitizes a wound image and models the digitized image into a set of printing instructions; a skin printing system further comprising an agar plate comprising the surface onto which the three-dimensional printer prints the skin product; a skin printing system wherein the three-dimensional printer is supplied with both a quantity of living skin cells from the patient with the imaged wound and a quantity of material not from the patient with the imaged wound (such as, e.g., collagen or another scaffold-building material as the non-patient material); a skin printing system further comprising a digitizer; and other inventive skin printing systems.

In another preferred embodiment, the invention provides an autograft treatment method of a wound of a patient, comprising: preparing the wound to be imaged; imaging the wound to obtain a set of images (such as, e.g., a wound imaging step that comprises photographing the wound); based on the set of images of the wound, modeling (such as, e.g., three-dimensional modeling) a skin graft product, wherein the modeling is performed by a computer, processor, or other machine; harvesting dermal cells from a donor site of the patient; from the harvested dermal cells, preparing a live cell suspension; loading a plate into a three-dimensional printer (such as, e.g., a printer-loading step that comprises loading an agar gel plate onto a platen of the printer); constructing a scaffold onto the plate (such as, e.g., a scaffold-constructing step in which the scaffold is constructed using little or none of the live cell suspension; a scaffold-constructing step that comprises constructing a scaffold of collagen (such as, e.g., bovine collagen (such as, e.g., Bovine Collagen Type 1)); etc.); seeding the scaffold with cells from the live cell suspension, until the modeled skin graft product has been constructed; when the skin graft product has been constructed, removing the skin graft product from the printer and from the plate; and after the removing step, placing the skin graft product in the wound; such as inventive methods wherein in the harvesting step, an amount of dermal cells harvested is in approximately a 1:5 ratio of skin harvested to skin estimated to be needed to treat the wound by conventional skin grafting; inventive methods wherein in the harvesting step, a maximum size is a 4 cm$^2$ split-thickness graft using standard dermatome techniques; inventive methods wherein in the harvesting step, an amount of dermal cells harvested is does not exceed a 1:5 ratio of cells harvested to cells estimated to be needed to treat the wound by conventional skin grafting; inventive methods comprising dissociating and culturing the harvested cells in a culture medium (such as methods comprising adding allogeneic fibroblasts and keratinocytes to the culture medium); inventive methods further comprising securing the skin graft product with sutures and covering the skin graft product with a bandage; inventive methods comprising constructing multiple skin graft products for a same wound; inventive methods comprising constructing a first skin graft product and a second skin graft product for a same wound, on different days; a method further comprising printing insulin into the skin graft product being constructed; a method further comprising printing or spraying amniotic membrane into the skin graft product being constructed; and other inventive methods.

In another preferred embodiment, the invention provides a skin graft product constructed from skin cells of a patient having a wound, wherein an amount of patient skin cells is less than the patient skin cells that would be estimated to be needed to treat the wound if only the patient skin cells were used, such as, e.g., an inventive skin graft product consisting of: an amount of patient skin cells which is less than the patient skill cells that would be estimated to be needed to treat the wound by conventional skin grafting if only the patient skin cells were used; and an amount of material other than patient skin cells; an inventive skin graft product wherein the amount of patient skin cells is selected from the group consisting of: about ⅔ what would be estimated to be needed to treat the wound if only the patient skin cells were used; less than ⅔ what would be estimated to be needed to treat the wound if only the patient skin cells were used; less than ½ what would be estimated to be needed to treat the wound if only the patient skin cells were used; less than ⅓ what would be estimated to be needed to treat the wound if only the patient skin cells were used; less than ¼ what would be estimated to be needed to treat the wound if only the patient skin cells were used; and less than ⅕ what would be estimated to be needed to treat the wound if only the patient skin cells were used; an inventive skin graft product wherein the amount of material other than patient skin cells comprises one or more of bovine collagen, growth factors, amniotic membrane and cytokines; and other inventive skin graft products.

In another preferred embodiment, the invention provides a method of treating a patient wound, comprising: constructing a set of custom skin graft products G1... Gn customized to the wound; placing the custom skin graft product G1 onto the wound; and placing the custom skin graft product Gn onto the custom skin graft product Gn–1 already placed on the wound, such as, e.g., an inventive method comprising layering custom skin graft products onto the wound over a period of days; and other inventive methods.

The invention in another preferred embodiment provides a method of avoiding wastage of dermal cells harvested for autografting to treat a wound of a patient, comprising: harvesting a quantity of skin cells from a non-wound site of the patient having the wound; processing all of the harvested quantity of skin cells into an autograft skin product without wasting or discarding any of the harvested quantity of skin cells (such as, e.g., a processing step that comprises three-dimensional printing of an irregular three-dimensional shape); and applying the autograft skin product onto the wound; such as, e.g., inventive methods further comprising meshing the autograft; inventive methods wherein a ratio of surface area of the wound to surface area of a harvest site is about 5 square inches of wound to 1 square inch of harvest site, which is expressed as a Wound/Harvest Areas Ratio of 5:1; inventive methods wherein a Wound/Harvest Areas Ratio is in a range of from 2:1 to 7:1; inventive methods wherein the Wound/Harvest Areas Ratio is in a range of from 5:1 to 7:1; and other inventive methods.

The invention in another preferred embodiment provides an auto-grafting method for treating a wound of a patient, comprising: harvesting a quantity of skin cells from a patient; and auto-grafting onto the wound of the patient the quantity of harvested skin cells, with the quantity of autografted harvested skin cells being substantially equal to the quantity of harvested skin cells (such as, e.g., an auto-grafting step that comprises auto-grafting a three-dimensional irregularly-shaped skin graft product); an auto-grafting method further comprising constructing, via operation of a three-dimensional printer, a skin graft product comprising the quantity of harvested skin cells; and other inventive auto-grafting methods.

DETAILED DESCRIPTION OF PREFERRED EMBODIMENT OF THE INVENTION

In a dermal autograft that comprises a quantity of harvested patient dermal cells, the invention advantageously minimizes the quantity of harvested patient dermal cells that are needed for an autograft to cover a particular wound. For such minimization, harvested patient dermal cells (preferably ALL of the harvested patient dermal cells) are used in combination with a quantity of material which is NOT harvested patient dermal cells, to construct a dermal autograft product to be applied to a wound. Preferred construction methods for use in the invention are, e.g., a layering method performed by a 3D printer (such as, e.g., 3D printer 1 in FIG. 1); a method in which a computerized skin printing system is used (such as a computerized skin printing system of FIG. 1, see Example 1 herein); etc.

A preferred example of material which is NOT harvested patient dermal cells and which is useable in the invention is collagen, such as, e.g., Bovine Collagen Type I; Collagen IV; etc. As to Collagen IV, see, e.g., M. Paulsson, "Basement Membrane Proteins: Structure, Assembly, and Cellular Interactions," *Critical Reviews in Biochemistry and Molecular Biology*, 27(½): 93-127 (1992).

The inventive methodology preferably is used to fabricate then print skin tissue using much smaller areas of donor skin (such as, e.g., no larger than 4 cm$^2$ split-thickness grafts harvested using standard dermatome techniques) compared to conventional methodology. The invention's provision of the ability to use such smaller areas of donor skin corresponds to a significant reduction in skin injury and subsequently less opportunity for transformation into a chronic wound or other sequelae common to donor sites. Advantageously, the invention provides an improved ratio of wound area to donor site (such as a 5:1 ratio of wound area to donor site; a 6:1 ratio of wound area to donor site; a 7:1 ratio of wound area to donor site; etc.) compared to a grafting methodology having a 1:1 up to 3:1 ratio of wound area to donor site for a mesh graft. Advantageously, the invention is useable for a relatively small area of donor site to cover relatively much wound site, such as, e.g., being able to cover 5-7 times, or more, of the donor site.

A preferred methodology of combining harvested patient dermal cells and other material which is NOT harvested patient dermal cells is for cells from the respective donor site and non-donor sources to be processed until ready for loading into a set of dispensers in a 3D printer, and the 3D printer is used to perform a printing process by which the patient dermal cells and other materials are printed into a unitary graft product.

To obtain the patient dermal cells, preferably small split thickness skin grafts are created and epidermal cells harvested, after which the heterogeneous mixture of cell types comprising mainly fibroblasts and keratinocytes is dissociated and cultured using standard cell culture techniques. Preferably, to stimulate rapid proliferation, allogeneic fibroblasts and keratinocytes are added to culture media along with a cocktail including appropriate growth factors.

In a preferred example of a printing process, autologous cells which have been incubated with allogeneic fibroblasts and keratinocytes are printed onto a bovine collagen matrix in the size, shape, and depth of the patient's particular wound. In a most preferred example, collagen is printed first, then skin cells are layered onto the collagen. Preferably the collagen matrix is fortified with growth factors, amniotic membrane, and specific cytokines which serve as an active extracellular matrix (ECM) and basement membrane structure. Such procedures are preferred in order to set in motion a process by which the partially autologous skin graft will mimic the architecture of the patient's own tissue.

Following preparation of the wound bed, a skin structure produced according to the invention is transplanted into the analogous structure of the wound.

An advantage of the invention is to use the patient's own skill cells to re-create a strong, persistent organ replacement solution.

Additionally, the time in which the replacement product is produced is much faster than the weeks needed to generate skin autografts produced in vitro using conventional methodology. The current state of the science has not reported manipulating cell proliferation at the rate needed for a 3-7 day growing phase. By contrast, advantageously, 3D cell printing according to the invention using an enhanced cell proliferation method with a mixture of cell types, ECM proteins, growth factors, and cytokines greatly reduces the time for regeneration of an adequate skin graft suitable for transplantation and healing.

Unlike skin substitutes such as the dermal matrices Alloderm (human cadaveric), Strattice, or Integra (porcine sources) which are cost prohibitive and can be immunoreactive, the invention advantageously is used to recreate or regenerate a patient's own skin, in the shape and depth analogous to the injury. The resulting graft is less expensive compared to the mentioned products and has a better chance to "take". Addition of allogeneic cells bolster and enhance proliferation of the patient's own fibroblasts and keratinocytes, and provide a source of constituents such as extracellular matrix and growth factors.

As may be further appreciated with reference to FIG. 3, an example of an inventive skin printing process is step-wise as follows:

1) Preparing 301 the wound 300 (e.g., NPWT—to manage exudate, reduce/eliminate infection, create vascularized granular bed of tissue).

2) Photographing 302 the wound 300.

3) Automatically modelling 303 the to-be-produced graft in 3D from the wound photo.

4) Obtaining 304 dermal cells from donor site (estimating a ratio, such as estimating a 1:5 ratio).

5) Preparing 305 a live cell suspension using the dermal cells from the donor site.

6) Loading 306 a plate (such as an agar plate) into a 3D printer (such as by loading an agar plate onto a platen of a 3D skin printer).

7) Physically rendering 307 an acellular dermal matrix (ADM) scaffold with collagen (such as pre-processed Bovin Collagen Type I).

Figure 3:
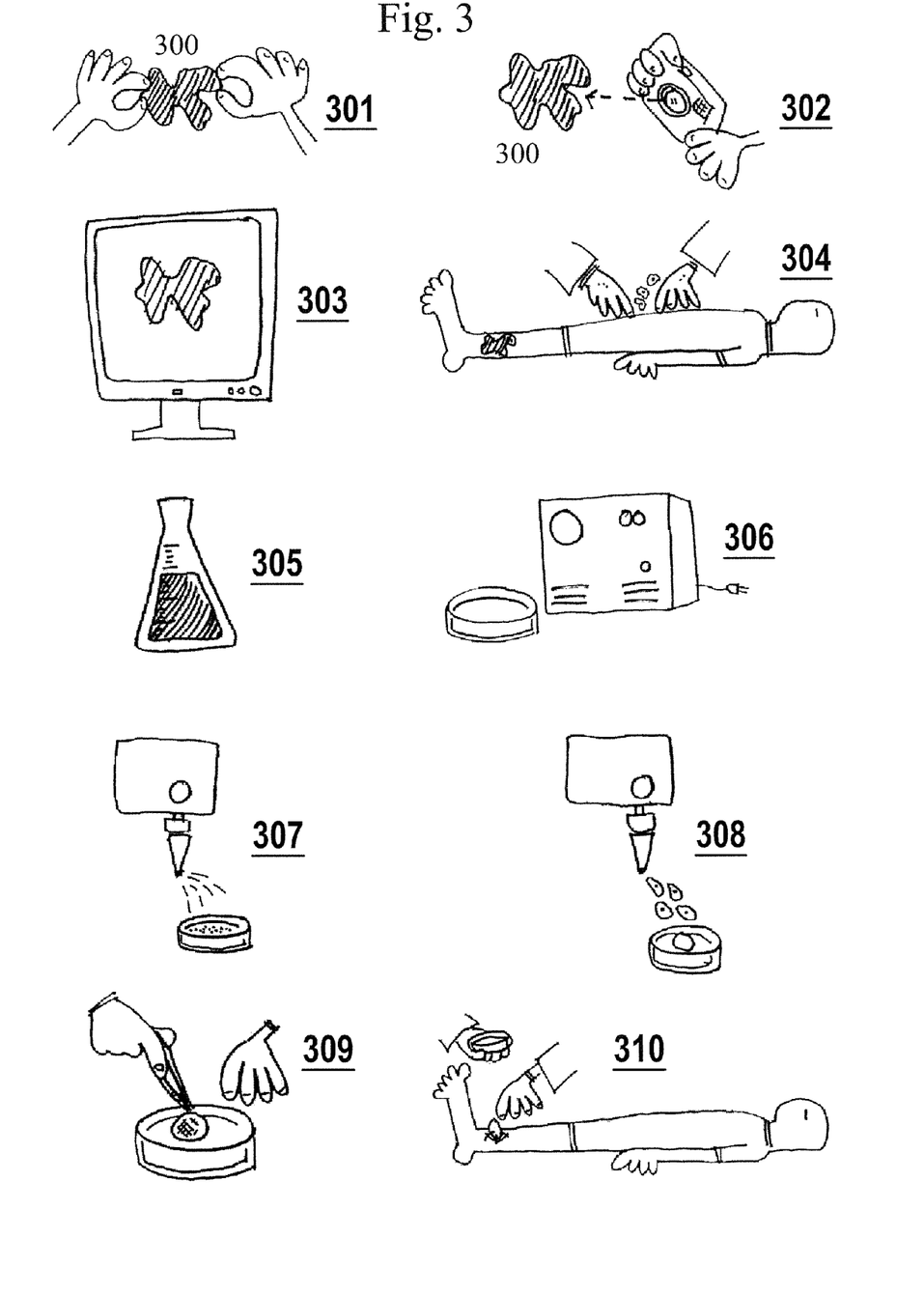
FIG. 3 is a diagram of steps in an inventive autologous gaffing method.

8) Seeding 308 the ADM scaffold with live cells processed from the autologous graft obtained in step 4 of this Example (step 304 in FIG. 3). Note, ADM may contain allogeneic fibroblasts. This step is also accomplished by "printing" the cells onto the ADM.

9) Removing 309 printed skin from the 3D printer and agar gel plate.

10) Performing a step 310 of placing the printed skin in the wound 300, securing with sutures and covering with a suitable bandage.

Figure 1:
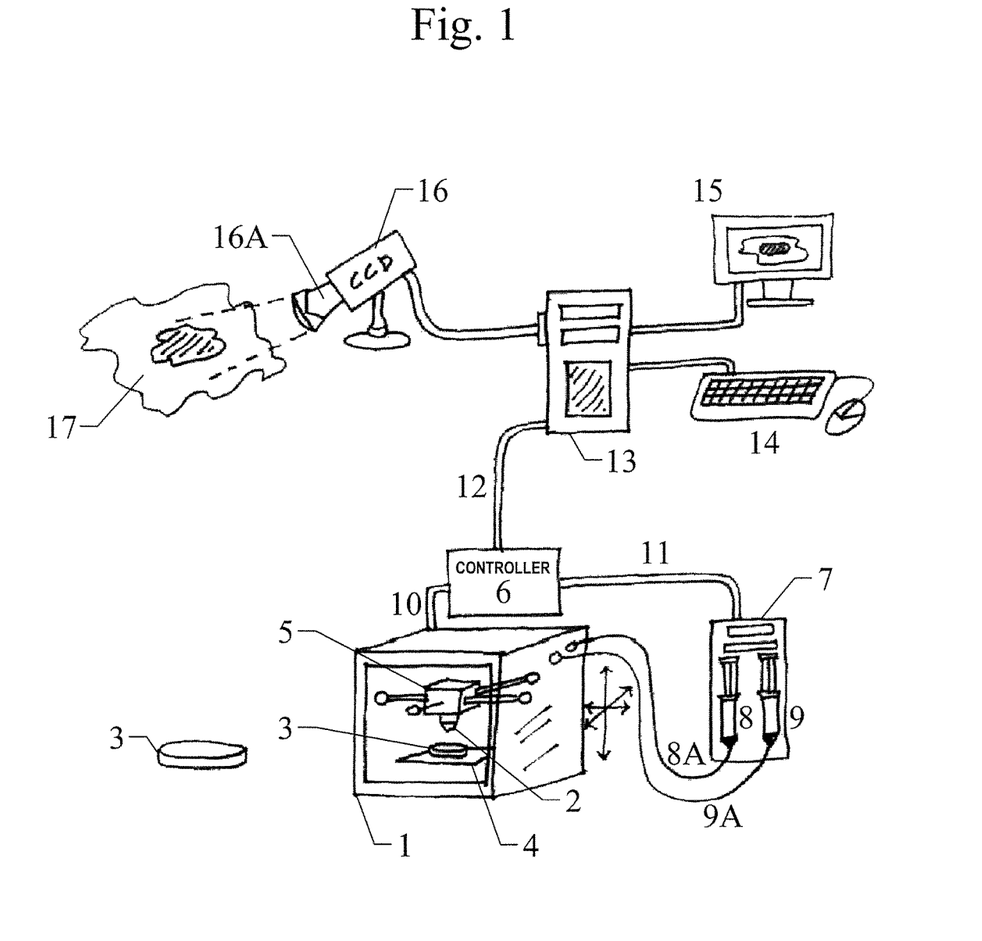
FIG. 1 is a diagram of a computerized skin printing system in an embodiment of the invention.
Figure 2:
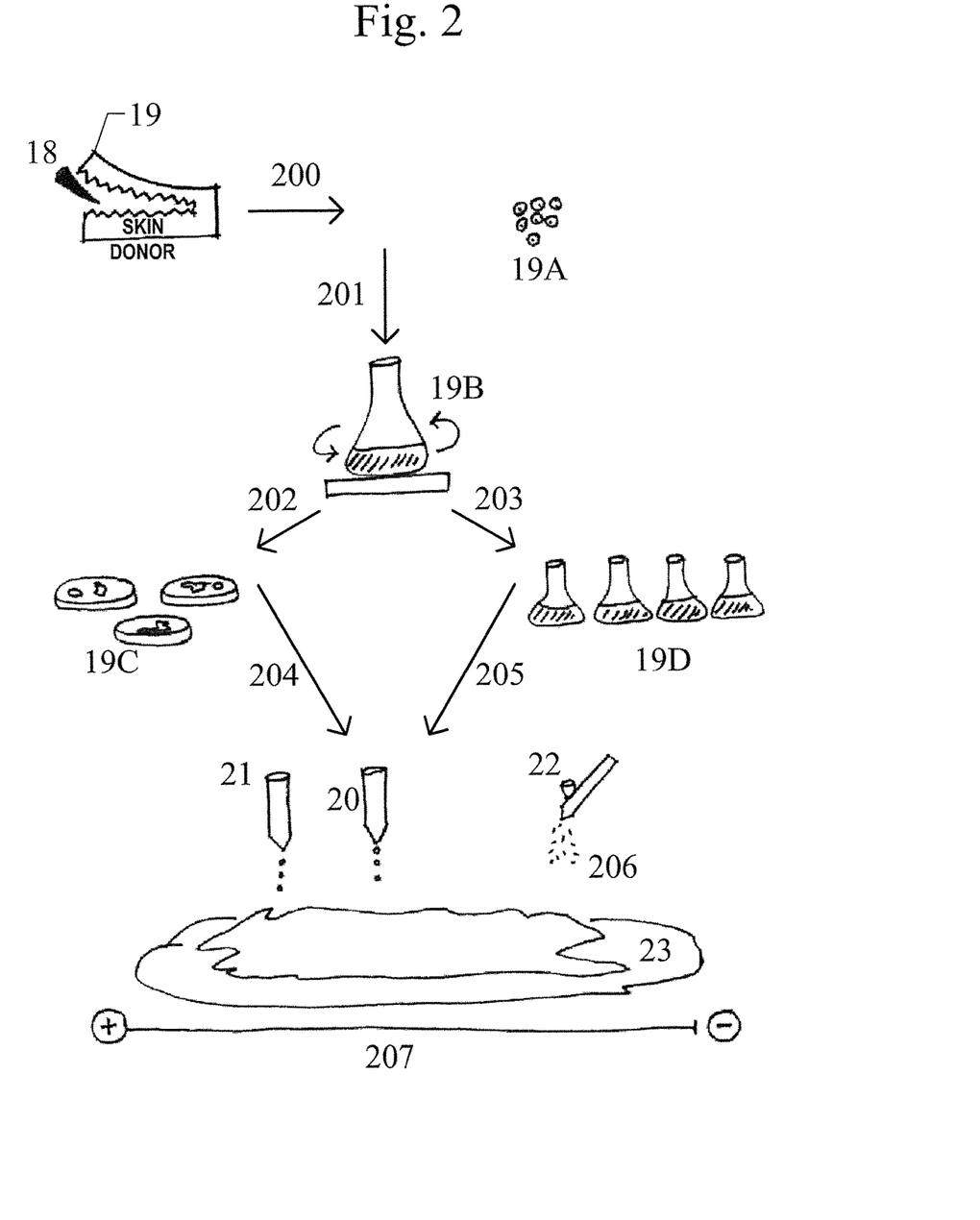
FIG. 2 is a diagram of an inventive method of producing an inventive autograft product, in an embodiment of the invention.

An inventive method of producing an inventive autograft product also can be appreciated with reference to FIG. 2. Surgical instrument 18 is used to separate epidermis 19 from skin at a donor site preferably of a same patient who has wound 17 (FIG. 1).

Separated epidermis 19 is processed 200 by enzymatic cell separation to produce separated dermal cells 19A which are dissolved 201 to produce a dermal cell solution 19B.

Dermal cell solution 19B is cultured 202 onto plates to provide plated dermal cells 19C and/or is split 203 into dermal cell solutions 19D (such as 70% confluency).

Cultured dermal cells 19C and dermal cell solutions 19D are harvested 204, 205 to be transferred to 3D printer cell dispensers such as dispenser 20.

Examples of contents of 3D printer cell dispenser 20 are, e.g., autologous fibroblasts, keratinocytes, ECM proteins, growth factors (GF s), cytokines. Examples of contents of 3D printer cell dispenser 21 are, e.g., GF, insulin, PDGF, eNOS. Examples of contents of 3D printer cell dispenser 22 are lyophyllized amniotic membrane.

A 3D printer (such as 3D printer 1 of FIG. 1) prints 206 the contents of the dispensers 20, 21, 22 onto a substrate 23 to produce a cultured graft preferably comprising bovine collagen, media, growth factors (GF s), etc.

Optionally an electrical field 207 is applied in a region of the substrate 23 during printing 206.

It will be appreciated that printing 206 from dispensers 20, 21, 22 is not required to be performed simultaneously and that printing 206 may be performed in various sequences.

An example of harvesting grafts is to harvest a first graft at 7 days (from when the epidermis was removed from the donor site), and to maintain other grafts unharvested for a period of time until needed through final closure.

The invention may be further appreciated with reference to the following examples, without the invention being limited thereto.

EXAMPLE 1

In one inventive example, as may be appreciated with reference to FIG. 1, an inventive computerized skin printing system comprises a three-dimensional (3D) printer 1. Preferably the 3D printer 1 is cooled or temperature-controlled. An example of a 3D printer 1 is a 3D printer capable of printing living cells. The 3D printer 1 comprises at least one dispenser head 2 from which emerges cells that are being printed onto a surface 3 (such as, e.g., an agar plate) which is accommodated on a platen 4 within the 3D printer. The dispenser head 2 is attached to print head 5 which is positionable in (x, y, z) dimensions, which positioning is controlled by controller 6. Controller 6 also controls a syringe pumping system 7.

Syringe pumping system 7 comprises syringe 8 in which is contained skin cells harvested from the patient for whom the auto-graft product is being made and syringe 9 in which is contained material which does NOT include the patient's skin cells, such as, e.g., bovine collagen; allogeneic skin cells; etc. System 7 optionally comprises static mixers. Syringes 8, 9 supply the 3D printer 1 via tubes 8A, 9A respectively. Components used by the 3D printer to print an auto-graft skin product are pumped from syringes 8, 9 to the dispenser head 2.

Controller 6 is electrically connected by electrical connection 10 to the 3D printer 1 and by electrical connection 11 to the pumping system 7.

Controller 6 is electrically connected via data line 12 to a computer 13. As an example of computer 13 is a computer comprising a digitizer, the computer having software loaded thereon such as, e.g., software that digitizes an image of a wound and models the defect for printing; software that digitizes an image of a wound and automatically detects wound boundaries and models the defect for printing; etc. In some embodiments, wound boundaries are manually detected. Computer 13 receives human operator input via an input device 14 which in FIG. 1 is illustrated as a keyboard but is not necessarily limited to a keyboard. A human operator reviews output from computer 13 on a monitor 15.

Components illustrated separately in FIG. 1, such as, e.g., input device 14 and monitor 15, are not necessarily required to be separate physical structures and can be integral with each other. Also, in FIG. 1, cables or connecting lines that are illustrated are not necessarily required in all embodiments to be physical structures and in some embodiments a wireless connection is provided.

Computer 13 is connected to an imaging device 16 such as, e.g., a camera. Preferably imaging device 16 delivers video images to computer 13. Imaging device 16 is positionable to image a wound on a living patient, such as, e.g., being positionable via a stable structure such as an articulated arm, tripod, cart or frame. Imaging device comprises a component 16A (such as, e.g., a lens) which in operation is positioned in a direction of a wound or other tissue defect 17. Preferably a sizing guide (such as, e.g., a sizing grid) is provided in a region of the wound 17 (such as, e.g., a laser grid for sizing) while the imaging device 16 is imaging the wound 17. Preferably a laser sizing grid is projected onto and/or near the wound 17 to provide data for sizing the wound. In another embodiment, graticulated markers are positioned proximate the wound to provide sizing information to the imaging device 16.

Preferably computer 13 performs steps of receiving a set of images taken by the imaging device 16 of the wound or tissue defect 17 and processing the imaged wound or tissue defect into a set of skin-printing instructions that are provided to the controller 6 connected to the 3D printer 1.

The system of FIG. 1 is useable to process a quantity of living donor skin cells harvested from a non-wound area of a patient having the wound or tissue defect 17.

EXAMPLE 2

Application of the dissociated cells and other agents by the 3D printer, specifically, the configuration of the cell dispenser/applicator/syringe/air-brush, is dependent upon the type and depth of the wound. The number of "layers" or "passes" the cell dispenser must take with each agent applied to the collagen matrix in this Example is at least one layer.

This approach of layering the patient's own fibroblasts, keratinocytes, etc., with commercially available amniotic membrane, growth factors, etc., is used to manipulate the healing process through wound supplementation with agents that are natural contributors to the wound healing process and specifically crucial for each particular wound type.

EXAMPLE 3

Examples of techniques are as follows.

Example 3.1

Following harvest of the donor site, individual cells of the epidermal layer are dissociated from the dermis. Dissociation of skin cells is accomplished by traditional trypsin: EDTA methods which is a preferable method for isolating keratinocytes from human skin. Human serum, bovine serum albumin, serum fibronectin, type IV collagen, and laminin added to traditional cell culture media provide support to the fibroblasts and keratinocytes. These basement membrane protein constituents form the layers of the extracellular matrix on which these epidermal and dermal cells grow. They are present in every tissue of the human body. They are always in close apposition to cells and it is well known that they not only provide structural support in the form of an organized scaffold, but they also provide functional input to influence cellular behavior such as adhesion, shape, migration, proliferation, and differentiation. Disassociated cells are incubated and continually shaken in cell culture flasks at 37° C. Cells are sub-cultured prior to confluency and allowed either to continue to proliferate in dissociated cell suspension flasks, plated on collagen plates to continue growth, or plated via the skin printer onto bovine collagen substrates.

Example 3.2

In this Example, a bovine collagen matrix is augmented with growth factors such as Platelet-Derived Growth Factor (PDGF), epidermal Nitric Oxide Synthase (eNOS), Vascular Endothelial Growth Factor (VEGF), and Tumor Necrosis Factor Beta (TNF-beta). Low-dose insulin is added to also promote cell growth and proliferation. Insulin is a powerful growth factor that has been used in animal and human clinical trials of wound healing. Insulin has been used as a topical agent to accelerate the rate of wound healing and the proportion of wounds that heal in diabetic animals and in humans. Treatment with insulin also increased expression of eNOS, VEGF, and SDF-lalpha in wounded skin. Rezvani conducted an RCT in diabetic foot wounds to evaluate topical insulin on healing in 45 patients. The mean rate of healing was 46.09 mm$^2$/day in the treatment group, and 32.24 mm$^2$/day in the control group (p=0.03). These data suggest that insulin can improve wound healing and may be beneficial when used in an in vitro model to increase cell proliferation and would enhance cell proliferation into the collagen matrix.

Example 3.3

3-4 days following the first application of autologous cells, and as the allogeneic cells and matrix begin to form obvious healthy epithelial tissue, lyophilized amniotic membrane (AM) is sprayed (such as from a modified airbrush-like apparatus (preferably associated with the print head of the 3D printer) onto the cell-seeded bovine collagen. There is a notable body of evidence to suggest that freeze-dried, powdered amniotic membrane promotes rapid healing and enhances the "take" rate of grafts. AM also inhibits natural inflammatory reactions which contribute to healthy tissue adhesion and structural development. There is evidence to suggest that combined with an electrical field, the application of AM will enhance cell migration and angiogenesis to cells located in the center-most region of the graft bed.

Example 3.4

Continual layers of the cultured material are printed onto collagen plates until desired thickness is achieved. Amount of cells wanted in each layer, number of times the printer must create layers for the skin graft, intervals between applications, and types and amounts of growth factors and other ECM proteins to be added are factors.

EXAMPLE 4

Multiple copies of the autograft are printed. (In this example, multiple copies are printed. It will be appreciated that in other cases due to limited donor site material there will only be enough to print one copy.) The first is transplanted to the primary wound within 5-7 days. During the 5-7 days preparation period, negative pressure wound therapy with or without simultaneous irrigation (e.g., saline) is applied to prepare the wound bed for graft acceptance as well as reduce bacterial load. Negative pressure therapy is known to induce angiogenesis and this increase in blood flow and the resultant delivery of nutrients not only to the wound bed but to the newly placed engineered craft is critical to its survival and success.

As was described hereinabove in the Background with respect to several studies conducted using amniotic membrane (AM) in both acute and chronic wounds, much of the first round placement was absorbed into the body. In some cases, it took as many of 3-4 full grafts of AM in order to result in full closure of the wound when using that conventional technology. By contrast, with skin printing according to the invention, a much thicker and partially autologous engineered graft that more closely approximates natural human skin is provided. A thicker, partially autologous engineered graft has improved probability of survival and ability to make active contributions to recruiting the active mechanisms of healing. Meanwhile, in practicing the invention, the additional skin grafts continue to mature and if necessary, are useable as the final step to closure. In the alternative, the graft copies could be stored in a tissue bank for later use by the same patient if, for example, additional surgical revisions were anticipated.

While the invention has been described in terms of a preferred embodiment, those skilled in the art will recognize that the invention can be practiced with modification within the spirit and scope of the appended claims.

What we claim as our invention is:

1. A computerized skin printing system comprising;
a quantity of living donor skin cells harvested from a non-wound area of a patient having a to-be-treated wound or tissue defect;
a three-dimensional printer that processes the quantity of living donor skin cells, wherein the three-dimensional printer is under control of a controller connected to the three-dimensional printer;
an imaging device;
a sizing grid projected onto the wound or tissue defect while the imaging device is being operated;
a computer that performs steps of receiving a set of images taken by the imaging device of the wound or tissue defect of the patient and processing the imaged wound or tissue defect into a set of skin-printing instructions that are provided to the controller connected to the three-dimensional printer, and operating the three-dimensional printer to construct a customized skin graft product useable to be auto-grafted onto the wound or tissue defect of the patient.

2. The skin printing system of claim 1, further comprising at least one syringe pump under control of the controller.

3. The skin printing system of claim 2, wherein the at least one syringe pump contains the quantity of living donor skin cells harvested from the non-wound area.

4. The skin printing system of claim 1, further comprising a surface onto which the three-dimensional printer prints a skin product.

5. The skin printing system of claim 4, wherein the skin product printed onto the surface corresponds to a model generated by the computer from the set of wound images.

6. The skin printing system of claim 1, further comprising a pump, and wherein skin cells in a syringe are pumped by the pump into the three-dimensional printer.

7. The skin printing system of claim 1, wherein the computer digitizes a wound image and models the digitized image into a set of printing instructions.

8. The skin printing system of claim 4, further comprising an agar plate comprising the surface onto which the three-dimensional printer prints the skin product.

* * * * *